(12) United States Patent
Rabello et al.

(10) Patent No.: US 7,955,402 B2
(45) Date of Patent: Jun. 7, 2011

(54) METHOD FOR RECYCLING AND EXPLOITATION OF THE GLYCERIN OBTAINED IN THE PRODUCTION OF BIODIESEL

(75) Inventors: Carlos Rene Klotz Rabello, Rio de Janeiro (BR); Bernardo Galvão Siqueira, Rio de Janeiro (BR); Raphael Bezerra De Menezes, Rio de Janeiro (BR)

(73) Assignee: Petroleo Brasileiro S.A. - Petrobras, Rio De Janeiro (BR)

( * ) Notice: Subject to any disclaimer, the term of this patent is extended or adjusted under 35 U.S.C. 154(b) by 470 days.

(21) Appl. No.: 12/000,154

(22) Filed: Dec. 10, 2007

(65) Prior Publication Data

US 2008/0295392 A1 Dec. 4, 2008

(30) Foreign Application Priority Data

Mar. 30, 2007 (BR) ...................................... 0701993

(51) Int. Cl.
*C10L 1/18* (2006.01)
(52) U.S. Cl. .......................................... 44/308; 568/869
(58) Field of Classification Search .................... 44/308; 568/869
See application file for complete search history.

(56) References Cited

U.S. PATENT DOCUMENTS 7,126,032 B1 * 10/2006 Aiken ........................... 568/869
7,718,833 B2 * 5/2010 Potthast et al. ............... 568/869
* cited by examiner

*Primary Examiner* — Cephia D Toomer
(74) *Attorney, Agent, or Firm* — Nixon & Vanderhye P.C.

(57) ABSTRACT

A method to exploit the glycerin obtained as a by-product of the industrial process to produce biodiesel inside or out of the industrial production unit, providing a reduction in the environmental liability that may be caused by an excess in the production of glycerin that cannot be exploited for industrial use. The referenced method uses recycling of the glycerin obtained through industrial process to produce biodiesel, using a process basically consisting of four stages: a) extracting glycerin produced as a by-product of the industrial process for producing biodiesel; b) hydrogenation of said n-propanol glycerin, c) recycling of the n-propanol thus obtained to be added to a mixture of alcohols; and d) transesterfication of the n-propanol mixture added to the alcohol mixture, together with raw material triglycerides from renewable sources in order to obtain biodiesel. The referenced recycling of the n-propanol stream provides a reduction in the amount of the alcohol mixture necessary for the industrial process to produce biodiesel, consequently reducing operational costs.

10 Claims, 2 Drawing Sheets

METHOD FOR RECYCLING AND EXPLOITATION OF THE GLYCERIN OBTAINED IN THE PRODUCTION OF BIODIESEL

CROSS REFERENCE TO RELATED APPLICATION

This application is based upon and incorporates by reference, the contents of Brazilian Patent Application No. PI 0701993-9 filed Mar. 30, 2007.

FIELD OF THE INVENTION

This invention refers to a method to exploit the glycerin produced as a by-product of the process used in biodiesel production.

More specifically, this invention refers to a method involving hydrogenation of said glycerin to produce a stream rich in n-propanol, and recycling of this n-propanol stream in the process used in biodiesel production.

FUNDAMENTALS OF THE INVENTION

Growing concerns about the environment and the ever more restrictive regulations to control environmental pollution have caused researchers to search for innovative and economically viable alternative raw materials to use in the industrial and energy production sector, for the purpose of obtaining raw materials to generate products that pollute less and that have biodegradable characteristics in comparison to those obtained from currently employed industrial technologies. This search for alternatives has opened many avenues of research in which the use of raw materials from renewable sources has been of particular interest.

In addition to environmental concerns, petroleum reserve depletion has encouraged research into the development of fuels of renewable origin to be used for transportation.

Biodiesel fuel is one of the candidates, which possesses fuel properties similar to conventional diesel fuel and is being used to reduce air pollution, to give new support to agriculture and to reduce dependence on fossil fuels, which are limited and in many cases are located in specific areas.

Using biodiesel fuels in conventional diesel motors results in a substantial reduction of unburned hydrocarbons, carbon monoxide, and particulate emissions into the environment.

Biodiesel fuel is considered a clean fuel and is free of sulfur and aromatics and carries around 10% in oxygen, which helps in its complete combustion.

Its high cetane number improves its quality of ignition as well as in mixtures with conventional diesel.

Brazil, due to its large expanse of territory, has in agriculture a factor of great importance in furtherance of its socio-economic development, and thus, objectifying the improvement of environmental conditions worldwide, which are being largely affected by economic activities of modern civilization, is promoting a big change in its energy sector structure by attempting to use renewable sources more and more frequently.

In this context, agricultural raw materials have been the object of rising interest, in as far as its exploration as new ways of utilization, in other words, as an insertion towards other traditional raw materials, make them economically attractive. Besides contributing to the improvement of the environment, it may serve as an extra source of resources in some Brazilian regions, and consequently may mean jobs for the local agricultural workforce.

Thus, there is a great effort in Brazil to make the use of raw vegetable materials viable in the energy sector as currently practiced in the country. In many cases, besides being economically more favorable, this raw material produces significant gains in the environment by giving rise to products that are less aggressive and less polluting to the environment, which has caused the development of new technologies, such as the production of biodiesel fuel.

However, together with the increase in biodiesel production, not only in Brazil but in much of the world, the amounts available of glycerin, a by-product of the process of the biodiesel fuel production, has significantly increased.

Thus, in some cases, the current markets using glycerin as raw material in their productive activities find they are not able, at least not at the moment, to absorb this significant increase in the available amount of glycerin.

Accordingly, as a by-product, glycerin has become an environmental liability, and this is more important mainly in more remote regions, due to the fact that they are not located near an industrial consumer.

For this reason, there is a concern not only as far as environmental questions involved, but also referring to an economical manner of consumption (and adding value) this consequent production of glycerin coming from the production of biodiesel.

RELATED TECHNIQUE

In the production of biodiesel, a mixture made up of renewal raw materials, which may be of vegetable origin (vegetable oils, of food grade or not), or of animal origin (tallow from cattle, goat, sheep, bird, etc.), is submitted to a reaction generally using an alcohol, where said alcohol is selected from methanol, ethanol, n-propanol, n-butanol, etc., preferably using a mixture of methanol and ethanol, which is used under the usual conditions for transesterfication, producing, in this way, a stream called biodiesel, and at the same time, generating glycerin as a by-product.

The glycerin thus produced as a by-product of the process of producing biodiesel has industrial applications generally known, therefore its use as a raw material for various industrial applications is not always found to be compatible and proper for use with its growing availability [sic]. In these cases, glycerin becomes an important environmental liability, which in addition to running up storage costs, may even, in some cases, make a biodiesel industrial plant financially not viable.

In a general way, in the technical literature available there are a great number of works on biodiesel using methanol and ethanol as raw materials for the transesterfication of triglycerides, and the subsequent production of glycerin; however, work is not found directed towards the exploitation of the by-product produced in biodiesel industrial production units that considers an integrated recycling process of the glycerin produced in the biodiesel production process in which are combined extracting stages of glycerin as by-product, hydrogenation of said glycerin to propanol, recycling the propanol thus produced to be mixed with methanol and/or ethanol, and the subsequent transesterfication of the propanol, methanol, and/or ethanol mixture together with triglycerides of animal and/or vegetable origin, to obtain biodiesel, in which the glycerin is used from the biodiesel itself to be recycled in the process after its hydrogenation, and now being in the form of an n-propanol chain, as presented by this invention.

SUMMARY OF THE INVENTION

The Units of Hydrogenation are characterized by a significant investment due to the need to use noble materials, robust equipment, high cost catalysts, and the proper systems to operate under high pressure.

In the case of large size industrial units for the production of biodiesel, this investment may become justifiable within their own facilities. However, as an alternative to take care of units of less capacity, the glycerin streams coming from these plants might be collected, stored, and processed jointly in one single unit of a sufficient size to justify the investment.

In any case, this invention presents the following advantages:
  Recyclability of the glycerin fraction produced as a by-product of biodiesel production;
  Use of the unaltered glycerin fraction (raw glycerin, such as it is obtained in industrial processing) for its hydrogenation to propanol; and
  Use of the same industrial equipments and operational processing conditions as those used for the production of biodiesel.

One of the objectives of this invention is the development of a method to exploit the glycerin obtained as a by-product of the industrial process for producing biodiesel inside or outside the industrial production unit, the recycling of which will reduce industrial biodiesel production costs. The above mentioned method includes a process which is basically composed of four stages:
  a) taking glycerin as a by-product of the industrial process for producing biodiesel;
  b) Hydrogenation of the glycerin through a stream rich in n-propanol;
  c) Recycling the n-propanol stream thus obtained to be added to an alcohol stream (methanol or ethanol); and
  d) Transesterfication of the n-propanol stream added to the alcohol (methanol or ethanol) stream, together with raw material triglycerides from renewable sources in order to obtain biodiesel.

For the purposes of this invention, the expression alcohol stream refers to a mixture of methanol and ethanol, and its composition in a combination that includes any reciprocal proportion, ranging from 0 to 100% between them.

Also for the purposes of this invention, the expression raw material triglycerides from renewable sources refers to a mixture of triglycerides of animal and vegetable origin, and its composition in a combination that includes any reciprocal proportion, ranging from 0 to 100% between them.

DETAILED DESCRIPTION OF THE INVENTION

To facilitate understanding of this invention, the method herein proposed is explained below in greater detail.

Figure 1:
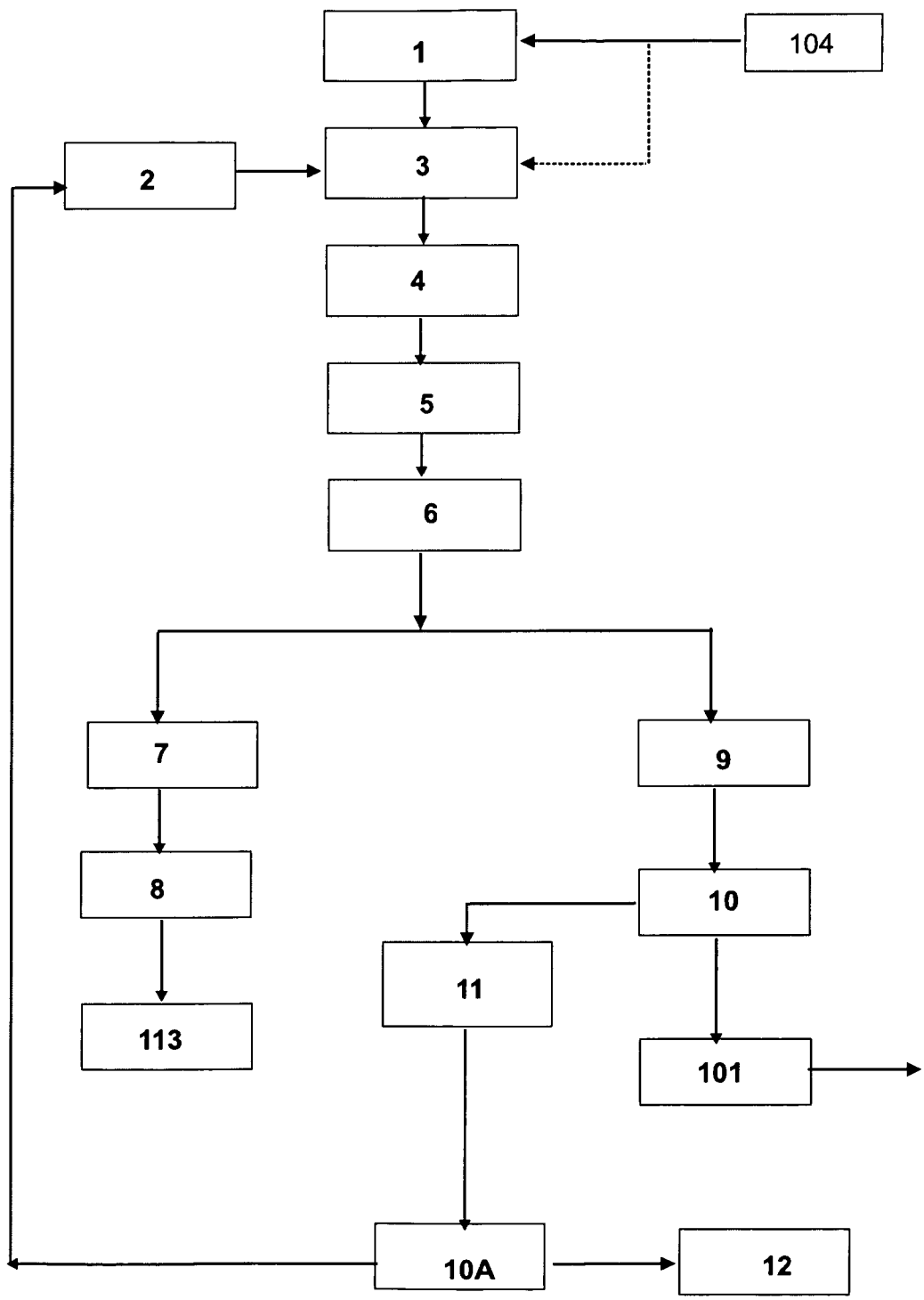
FIG. 1 shows a schematic representation of a classic biodiesel production process.

FIG. 1 is a schematic representation of the biodiesel production process. A mixture of triglycerides (1) and alcohol (2), generally methanol and/or ethanol, are submitted to a transesterfication reaction in one (3) or more stages (4), followed by washing (5) and separation (6). A stream containing raw biodiesel (7) is recovered in the separation (6) which is purified (8), obtaining thusly a biodiesel stream (113) and another stream containing raw glycerin (9) which will be distilled (10), recovering glycerin (101) and a mixture of methanol and water (11), which shall be distilled another time (10A) to separate from the water (12) to be reused as a raw material.

Figure 2:
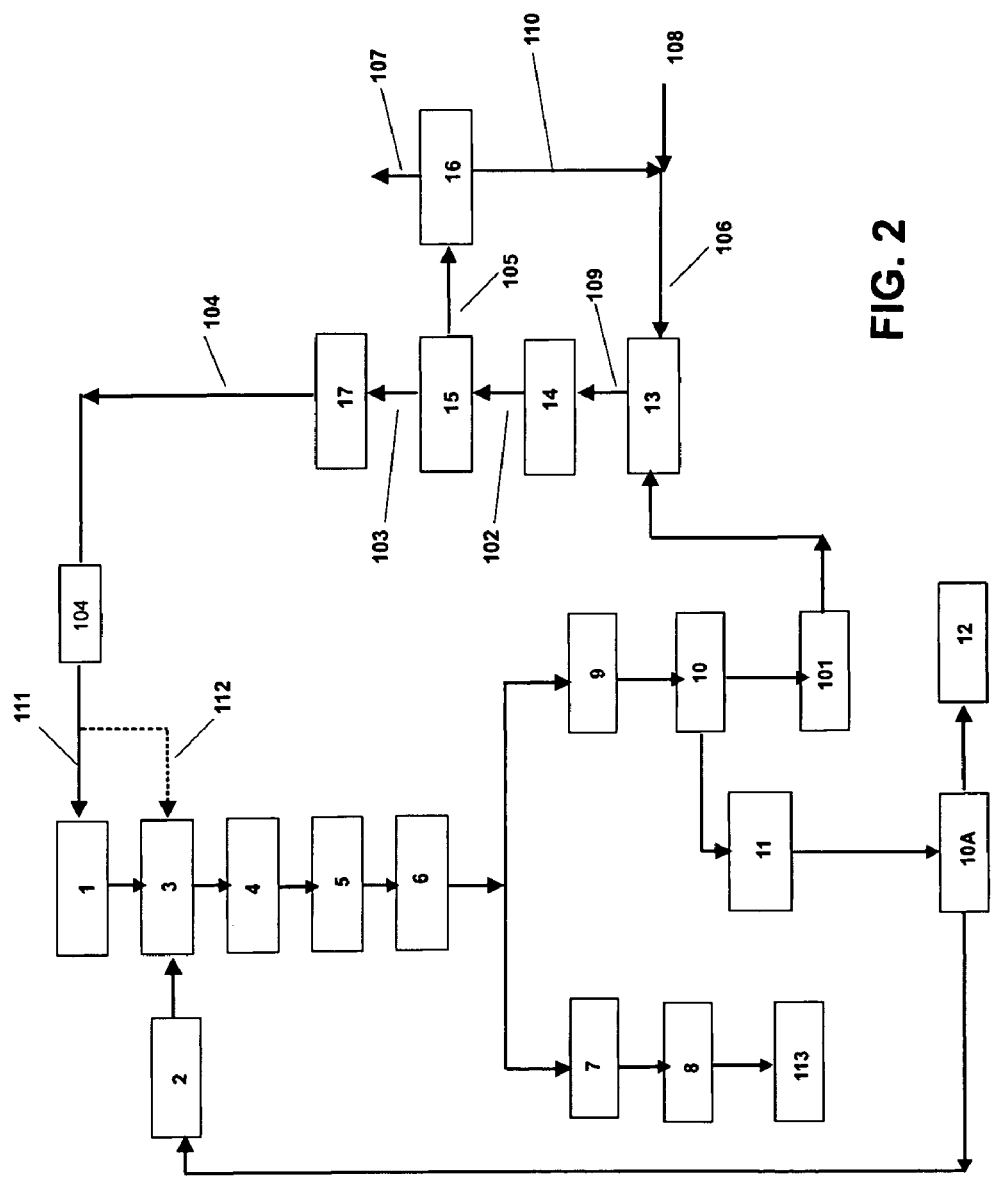
FIG. 2 shows a simplified schematic diagram of a biodiesel production unit, coupled to a proposal of a unit of hydrogenation of glycerin to n-propanol.

FIG. 2 is a schematic representation of the method to exploit the glycerin, the object of this invention, which in a general way, includes for basic stages:
  a) Glycerin extraction,
  b) Glycerin hydrogenation,
  c) The n-propanol obtained is recycled, and,
  d) Transesterfication of the reagents.

In the first stage (glycerin extractation), the glycerin obtained as a by-product of the industrial process to produce biodiesel is separated for later treatment.

In the second stage (hydrogenation), the glycerin produced in the industrial process to produce biodiesel is hydrogenated using the supported (usual) metal catalyst, with high selectivity to n-propanol. In this stage, besides the n-propanol, other alcohols are formed, such as methanol, ethanol, and isopropanol, and depending on the catalyst used in hydrogenation and on the quality of the glycerin, there may be a need for additional purification of the raw glycerin before the hydrogenation stage.

In the third stage (recycling) the n-propanol stream thus obtained is recycled and mixed with methanol and/or ethanol, which are the customary components used in conventional processes.

In the fourth stage (transesterfication), the n-propanol, methanol and/or ethanol stream produced is reacted with triglycerides from renewable raw materials that may be of vegetable (vegetable oils), or animal (tallow from cattle, goat, sheep, bird, etc.), origin.

These mixtures of the referenced raw materials originating from renewable sources may be a compound of several raw materials from renewable sources that include a combination in any reciprocal proportion, ranging from 0 to 100% between them, since the final compound must satisfy the essential requirements for good execution of the industrial process to produce biodiesel.

From this transesterfication reaction esters are obtained, mainly propyl esters, with properties very similar to conventional biodiesel (methyl and ethyl esters). Propyl esters confer an increase in the cetane number to the final biodiesel. The other alcohols present (methanol and ethanol), which are produced in the hydrogenolysis of the glycerin, also will react, forming more product.

As alcohol chain increases, the transesterfication reaction rate becomes slower, which leads to more severe operational conditions and a longer residence time to obtain conversions which are compatible with the original process. An alternative solution is to add more stages to the reaction.

Depending on the alcohol used as raw material, (methanol or ethanol), the final product of this integrated hydrogenation/transesterfication process will generate a biodiesel compound of methyl or ethyl and propyl esters.

Recycling of glycerin in the form of an n-propanol stream to the biodiesel production flows reduces the addition of methanol and/or ethanol usually employed for biodiesel production, as in the case of using methanol, said recycling has as a consequence a reduction of imports, since Brazil imports methanol.

Alternately, the n-propanol stream obtained, in its entirety or in part, may be used as an oxygenated solvent for several applications.

With this invention, the glycerin produced in the industrial process to produce biodiesel may be hydrogenated until it disappears to produce an n-propanol stream that is utilized directly in the process, generating a maximization of production.

Preferred Methods of Implementation

The glycerin stream (101), which is a by-product of the industrial biodiesel production unit, is directed towards the hydrogenation system, made up of one or more serial reactors (not shown in the Figure) containing hydrogenation catalyst.

Depending on the catalyst used and the level of contaminants in the glycerin, this stream may need additional purification before being sent to the hydrogenation stage.

The reactors may be of the trickle bed, mixed or batch type, and even adiabatic, isothermal or not isothermal and not adiabatic, with recycling or not.

The use of more than one reactor is linked directly to the conversion and to the efficiency desired per pass and to the thermal exchange system.

Together with the stream (101), a stream composed basically of hydrogen (109) coming from the compression system (13), is also allowed into the reaction system.

During the hydrogenation stage (14), a large part of the glycerin (101) is converted to n-propanol, generating water and a small amount of by-products such as methanol and ethanol (hydrogenolysis) and traces of light hydrocarbons and other oxygenated products.

The hydrogenated product (102) is submitted to a "flash" (15) type separation to recover hydrogen and to separate light hydrocarbons formed generating the stream (105). This stream (105) goes through a purge (16) producing a stream (107) that is sent to be burned off to avoid the accumulation of inert elements in the system, and the hydrogen stream (110). To this stream (110) is added the "make-up" stream (108), which may be basically defined as the amount of hydrogen consumed in the hydrogenation stage (14). The resulting hydrogen stream (106) is sent to the compression system (13).

The product (103), which results from the separation stage (15) after removing the light compounds, passes to the dehydration stage (17), in order to remove the water formed in the reactional stage, and to recover the n-propanol (104). The water must be removed because acts in order to reduce the conversion of the esterification stage of the triglycerides.

After dehydration (17), the n-propanol stream (104), composed of n-propanol, methanol, ethanol, and traces of oxygenated products, is directed towards the esterification stages. This n-propanol stream may be allowed into the first stage (stream 111), or in the subsequent stages (stream 112), or in more than one stage at the same time. This n-propanol stream, when used in the esterification of triglycerides, will produce propyl esters that work to reduce the consumption of methanol and/or ethanol and even provide an increase in the cetane number of the biodiesel stream. The biodiesel obtained (113) will be a mixture of methyl, ethyl, and propyl esters.

The glycerin may be recycled in the hydrogenation stage in order to form n-propanol until it is eliminated or according to the demands of the market for glycerin be satisfied.

Along this same line, the n-propanol stream (104) may be sent to the esterification process or may be separated out to be commercialized, for example, as an oxygenated solvent.

Recycling the n-propanol stream thus obtained may reduce the addition of new methanol and/or ethanol in the industrial process operation, which provides a saving greater than 25% of load of methanol and/or ethanol added Some examples are given below for the sole purpose of illustrating the invention, without implying any limitation to same.

Example 1

Glycerin was hydrogenated in the presence of a noble metal catalyst containing 0.48% Pd and 0.15% Pt supported in alumina, in a PAAR reactor of the batch type.

The reactor contains a basket where it is possible to place the catalyst to facilitate separation and to avoid its break during the test. Initially, 10 ml of the catalyst was placed in the basket.

The system was evacuated and purged with hydrogen three times to remove any air existing in the interior.

Later, the catalyst went through a 4 hour pre-treatment with 99.999% hydrogen, at 35 kgf/cm$^2$ at 300° C., for the purpose of reducing the metal deposited. At the end of this stage, the reactor was cooled up to 100° C. and 200 ml of glycerin was introduced, through a pressurized stainless steel cylinder. Finally, the system is heated once again up to 240° C. and is pressurized with hydrogen up to 35 kgf/cm$^2$. The time of reaction was 12 hours under stirring of 1,000 rpm. At the end of the test, the reactor was cooled, depressurized and opened.

A sample of the flow indicated by (103) in the diagram in FIG. 1, was analyzed, obtaining a glycerol conversion on the order of 89.32%. The composition of the product is found described in Table 1.

TABLE 1

| Sample (stream 103) | Level (% P/P) |
|---|---|
| Methanol | 0.89 |
| Ethanol | 1.90 |
| Isopropanol | 1.68 |
| n-Propanol | 79.40 |
| Propylene Glycols | 6.44 |
| Not Identified | 9.69 |
| TOTAL | 100.00 |

Example 2

In this example, refined soybean oil was used in the reaction with methanol in the presence of KOH. Taking as a base the product obtained in Example 1, considering that the conversion of the raw material was total (for example, soybean oil) and the recycling of the hydrogenated stream was performed until the alcohols present were eliminated, an analysis of the final composition of the biodiesel (stream 113 in the Figure) was made. The composition is shown in Table 2.

TABLE 2

| Sample (stream 113) | Level (% P/P) |
|---|---|
| Methyl Esters | 74.11 |
| Ethyl Esters | 0.27 |
| Propyl Esters | 25.23 |
| Glycerin | 0.35 |
| Methanol | 0.01 |
| n-Propanol | 0.01 |
| Not Identified | 0.02 |
| TOTAL | 100.00 |
| Glycerol Conversion | 89.32% |
| Selectivity to n-Propanol | 79.40% |

In spite of the fact that this invention has been illustrated in a representative manner by the examples presented, it is not limited to these, and it will be understood by those that are versed in the technology that it may be implemented under a broad range of conditions, formulations, and other equivalent parameters, without obviating the spirit or scope of the context of this invention, which are outlined in the Claims.

The invention claimed is:

1. Method for recycling and exploitation of the glycerin obtained in the production of biodiesel, the method comprising the steps of:
    (a) extracting glycerin produced as a by-product of the industrial process for producing biodiesel;
    (b) hydrogenating glycerin through a stream rich in n-propanol;
    (c) recycling of the n-propanol stream thus obtained to be added to an alcohol stream comprising methanol or ethanol; and
    (d) transesterfying the n-propanol stream added to the alcohol stream, together with raw material triglycerides from renewable sources in order to obtain biodiesel.

2. Method for recycling and exploitation of the glycerin obtained in the
    production of biodiesel, in accordance with claim 1, wherein the referenced alcohol stream comprises a mixture of methanol and ethanol, wherein the mixture comprises greater than 0% and less than 100% methanol and the mixture comprises greater than 0% and less than 100% ethanol.

3. Method for recycling and exploitation of the glycerin obtained in the production of biodiesel, in accordance with claim 1, wherein the referenced triglyceride raw material from renewable sources be made up of a compound of triglycerides of vegetable and animal origin wherein the compound comprises greater than 0% and less than 100% triglycerides of vegetable origin and the compound comprises greater than 0% and less than 100% triglycerides of animal origin.

4. Method for recycling and exploitation of the glycerin obtained in the production of biodiesel, in accordance with claim 3, wherein the referenced triglyceride raw material of vegetable origin be made up of a composition of vegetable oils.

5. Method for recycling and exploitation of the glycerin obtained in the production of biodiesel, in accordance with claim 3, wherein the triglyceride raw material of animal origin be a composition of animal tallow.

6. Method for recycling and exploitation of the glycerin obtained in the production of biodiesel, in accordance with claim 1, wherein the stages of the referenced method utilize the same equipment used for the industrial process to produce biodiesel and be performed under the same operational conditions as the industrial process to produce biodiesel.

7. Method for recycling and exploitation of the glycerin obtained in the production of biodiesel, in accordance with claim 1, wherein the referenced extraction of glycerin produced as a by-product of the industrial process to produce biodiesel include the use of the raw glycerin fraction for hydrogenation of the glycerin in a stream rich in n-propanol.

8. Method for recycling and exploitation of the glycerin obtained in the production of biodiesel, in accordance with claim 1, wherein the referenced recycling of the n-propanol stream substitute part of the referenced alcohol stream comprising methanol or ethanol providing a reduction in the amount of alcohol mixture necessary for the method.

9. Method for recycling and exploitation of the glycerin obtained in the production of biodiesel, in accordance with claim 8, wherein the referenced reduction in the amount of alcohol mixture necessary is in excess of 25%.

10. Method for recycling and exploitation of the glycerin obtained in the production of biodiesel, in accordance with claim 5, wherein the composition of animal tallow is obtained from cattle, goat, sheep, bird, or a mixture thereof.

* * * * *